(12) United States Patent
Notelovitz (10) Patent No.: US 6,901,278 B1
(45) Date of Patent: May 31, 2005

(54) METHODS FOR REDUCING THE RISK OF BREAST CANCER IN AND IMPROVING THE HEALTH OF WOMEN

(76) Inventor: Morris Notelovitz, 4279 NW. 61$^{st}$ La., Boca Raton, FL (US) 33496

( * ) Notice: Subject to any disclaimer, the term of this patent is extended or adjusted under 35 U.S.C. 154(b) by 304 days.

(21) Appl. No.: 10/354,238

(22) Filed: Jan. 29, 2003

Related U.S. Application Data (60) Provisional application No. 60/352,997, filed on Jan. 29, 2002.

(51) Int. Cl.$^7$ ................................................ A61B 5/00
(52) U.S. Cl. ...................... 600/407; 600/425; 600/427; 600/437; 600/443; 600/562; 378/37; 436/63; 435/4
(58) Field of Search ................................ 600/407, 425, 600/427, 437, 443, 562; 378/37; 436/63, 64; 435/4

(56) References Cited

PUBLICATIONS

Boyd, N.F. et al. (Sep. 19, 2002) "Heritability of Mammorgraphic Density, A Risk Factor for Breast Cancer," *N. Engl. J. Med.* 347(12):886–894.

Cauley, J.A. et al. (Feb. 16, 1999) "Elevated Serum Estradiol and Testosterone Concentrations are Associated with a High Risk for Breast Cancer. Study of Osteoporotic Fractures Research Group," *Ann. Intern. Med.* 130(4 Pt 1):270–277.

Clemons, M. and P. Gross (Jan. 25, 2001) "Estrogen and the Risk of Breast Cancer" *N. Engl. J. Med.* 344(4):276–285.

Beral, V. et al. (Collaborative Group on Hormonal Factors in Breast Cancer, Oct. 11, 1997) *Lancet*, 350:1047–1059.

Cushman, M. et al. (Jun. 1, 1995) "Synthesis, Antitubulin and Antimitotic Activity, and Cytotoxicity of Analogs of 2–methoxyestradiol, an Endogenous Mammalian Metabolite of Estradiol that Inhibits Tubulin Polymerization by Binding to the Colchicine Binding Site" *J. Med. Chem.* 38:2041–2049.

Fotsis, J. et al. (Mar. 17, 1994) "2–methoxyestradiol, an Endogenous Estrogen Metabolite, Inhibits Angiogensis and Suppresses Tumor Growth," *Nature* 368:237–239.

Gajdos, C. et al. (Apr. 2000) "Breast Cancer Diagnosed During Hormone Replacement Therapy" *Obstet. Gynecol.* 95(4):513:518.

Gapstur, S.M. et al. (Jun. 9, 1999) "Hormone Replacement Therapy and Risk of Breast Cancer with a Favorable Histology: Results of the Iowa Women's Health Study" *JAMA* 281(22):2091–2097.

Guttmacher, A.E. and F.S. Collins (Nov. 7, 2002) "Genomic Medicine—a Primer" *N. Eng. J. Med.* 347(19):1512–1520.

(Continued)

*Primary Examiner*—Ruth S. Smith
(74) *Attorney, Agent, or Firm*—Saliwanchik, Lloyd & Saliwanchik (57) ABSTRACT

The subject invention provides methods for evaluating women in designing appropriate menopausal and postmenopausal therapies to match the particular needs of the individual. In one embodiment, the subject invention provides methods for evaluating particular factors in menopausal and postmenopausal women that are then taken into account in identifying a therapy program to promote good health and reduce the risk of any adverse health effects as a result of the therapy, specifically the role of hormone induced/associated breast cancer. More specifically, the subject invention includes methods for evaluating menopausal and postmenopausal women to determine whether hormone replacement therapy is appropriate in this regard, and if so, the specifics of how that therapy is to be administered. The subject invention, by incorporating various factors into a comprehensive, function breast hormone profile, allows for the identification of untreated women with estrogen-related metabolic abnormalities that may increase the risk of breast cancer. The subject invention determines specific therapies to correct and/or inhibit the aberrant biosynthetic pathways, and thus, the risk of cancer.

32 Claims, 5 Drawing Sheets

PUBLICATIONS

Hayes et al. (Sep. 1996) "17 Beta–Estradiol Hydroxylation Catalyzed by Human Cytochrome p450 1B1" *Proc. Natl. Acad. Sci. U.S.A.*, 93:9776–9781.

Huang et al. (Oct. 1, 1999) "Breast Cancer Risk Associated With Genotype Polymorphism of the Estrogen–Metabolizing Genes CYP17, CYP1A1, and COMT: A Multigenic Study on Cancer Susceptibility" *Cancer Res.* 59:4870–4875.

Kristensen VN (Feb. 2001) et al. "High–Throughput Methods for Dection of Genetic Variation" *BioTechniques* 30(2):318–332.

Lavigne et al. (Dec. 15, 1997) "An Association Between the Allele Coding for a Low Activity Variant of Catechol–O–Methyltransferase and the Risk for Breast Cancer" *Cancer Res.* 57:5493–5497.

Lieber, J.G. et al. (Jun. 20, 1995) "Adenovirus–Mediated Urokinase Gene Transfer Indues Liver Regeneration and Allows for Efficient Retrovirus Transduction of Hepatocytes in vivo" *Proc. Natl. Acad. Sci. U.S.A.* 92(13):6210–6214.

Lippert, T.H. et al. (1998) "Estradiol Metabolism During Oral and Transdermal Estradiol Replacement Therapy in Postmenopausal Women" *Horm. Metab. Res.* 30(9):598–600.

Lobo, R.A. (Mar. 1987) "Androgen Excess and the Infertile Woman" *Obstet. Gynecol. Clin. North Am.* 14(1):143–167.

Nebert, D.W. and D.W. Russell, "Clinical Importance of the Cytochromes P450," *Lancet*, Oct. 12, 2002, pp. 1155–1162, vol. 360.

Pasqualini, J.R.. et al. (1996) "Concentrations of Estrone, Estradiol, and Estrone Sulfate and Evaluation of Sulfatase and Aromatase Activities in Pre– and Postmenopausal Breast Cancer Patients" *J. Clin. Endocrinol. Metab.* 81(4):1460–1464.

Ruder, Henry J. et al. (1972) "Estrone Sulfate: Production Rate and Metabolism in Man" *J. Clin. Invest.* 51:1020–1023.

Siegelmann–Danieli, N. and K.H. Butetow (1999) "Constitutional Genetic Variation at the Human Aromatase Gene (Cyp19) and Breast Cancer Risk" *Br. J. Cancer* 79(3/4):456–463.

Ursin et al. (Jun. 16, 1999) "Urinary 2–Hydroxyestrone/16alpha–Hydroxyestrone Ratio and Risk of Breast Cancer in Postmenopausal Women" *J. Natl. Cancer Inst.* 9(12):1067–1072.

van de Vijver et al. (Dec. 19, 2002) "A Gene–Expression Signature as a Predictor of Survival in Breast Cancer" *N. Engl. J. Med.* 347(25):1999–2009.

Vehkavaara, S. et al. (Nov. 28, 2000) "Differential Effects of Oral and Transdermal Estogen Replacement Therapy on Endothelial Function in Postmenopausal Women" *Circulation* 102:2687–2693.

Vermeulen, A. et al. (1986) (Proc. of the XII International Study Group for Steroid Hormones, Rome, Dec. 2–4, 1985) "Steroid Dynamics in the Normal and Carcinomatous Mammary Gland" *J. Steroid Biochem.* 25:799–802, vol. 25.

West, M. et al. (Sep. 25, 2001) "Predicting the Clinical Status of Human Breast Cancer by Using Gene Expression Profiles" *Proc. Natl. Acad. Sci.* 98(20):11462–11467.

Zhu, B.J. and A.H. Conney (1998) "Functional Role of Estrogen Metabolism in Target Cells: Review and Perspectives," *Carcinogenisis* 19)1):1–27.

METHODS FOR REDUCING THE RISK OF BREAST CANCER IN AND IMPROVING THE HEALTH OF WOMEN

CROSS-REFERENCE TO RELATED APPLICATION

This application claims the benefit of U.S. Provisional Application Ser. No. 60/352,997, filed Jan. 29, 2002.

FIELD OF THE INVENTION

The present invention relates to methods for evaluating women to ascertain breast estrogen/hormone-related function so that appropriate menopausal and postmenopausal therapies that promote good health can be prescribed, and that adverse health events, including breast cancer, can be avoided or minimized.

BACKGROUND OF INVENTION

Menopause is a biological process in which a woman's ovaries reduce but do not completely stop their production of female sex hormones. Menopause is diagnosed when menstruation ceases permanently. Changing levels of female sex hormones that precede and postdate menopause often cause a variety of symptoms. Common health issues related to the menopausal transition and menopause include: irregular periods, hot flashes, increased risk of vaginal and/or bladder infection, urge incontinence, stress incontinence, fatigue, depression, loss of muscle mass, increased fat tissue, thinning and loss of skin elasticity, loss of bone tissue, impaired cognition, and an increased prevalence of cardiovascular disease.

One therapy used to combat symptoms associated with changing levels of female sex hormones is hormone replacement therapy (HRT). HRT is the administration of the female hormones including estrogen, progesterone, and androgens. One form of HRT is estrogen replacement therapy (ERT), which is the administration of estrogen alone. It is believed that HRT and ERT help in relieving symptoms of menopause and can be used to combat osteoporosis and to prevent the early onset of heart disease, two conditions often associated with postmenopause.

The long term benefits of HRT and ERT, however, remain questionable due to concerns regarding safety and efficacy. For example, HRT and/or ERT may increase an individual's risk of developing cancer. Specifically, it has been reported that prolonged exposure of the breast tissue to estrogen for five or more years of exogenous ERT is linked to an increased risk of breast cancer (Collaborative Group on Hormonal Factors in Breast Cancer, *Lancet*, 350:1047–1059).

It is believed that estrogen biosynthesis and function play an important role in the pathogenesis of certain cancers. This is true for breast cancer and is clinically correlated with the prevalence of breast cancer in women with evidence of increased endogenous estradiol synthesis. Thus, women with increased mammographic breast density, a clinical manifestation of excessive breast tissue estrogen synthesis, are at a higher risk of breast cancer (Boyd, N. F. et al., "Heritability of mammographic density, a risk factor for breast cancer," *N. Engl. J. Med.*, 347(12):886–94 (2002)) as are women with levels of serum estradiol levels in the upper quartile, than postmenopausal women with normal serum estradiol levels in the lower quartile (Cauley, J. A. et al., "Elevated serum estradiol and testosterone concentrations are associated with a high risk for breast cancer. Study of Osteoporotic Fractures Research Group," *Ann. Intern. Med.*, 130(4 Pt 1):270–7 (1999)).

The extent to which exogenous estrogen contributes to this pathology is not precisely established, but may be influenced by an individual's predisposition to cancer, by pathways of estrogen metabolism and catabolism, or by the route and dose of ERT or HRT. Breast cancer has well-defined histological criteria, but the etiology and pathogenesis of the cancer is varied for each histological type. In this context, the diagnosis of 'breast cancer' can be thought of as a syndrome, with cancers of varying degrees of differentiation, in which estrogen biosynthesis and function play a role. This is true for both endogenous estrogen production and estrogen replacement therapy (ERT) (Clemons, M. and P. Gross, "Estrogen and the risk of breast cancer," *N. Engl. J. Med.* 344:276–285 (2001)). Significantly, the HRT-related increase in breast cancer is most frequently associated with invasive breast cancer having a favorable histology (Gapstur, S. M. et al., "Hormone replacement therapy and risk of breast cancer with a favorable histology: results of the Iowa Women's Health Study," *JAMA*, 281(22):2091–7 (1999)) and prognosis (Gajdos, C. et al., "Breast cancer diagnosed during hormone replacement therapy," *Obstet. Gynecol.*, 95(4):513–8 (2000)).

Figure 1:
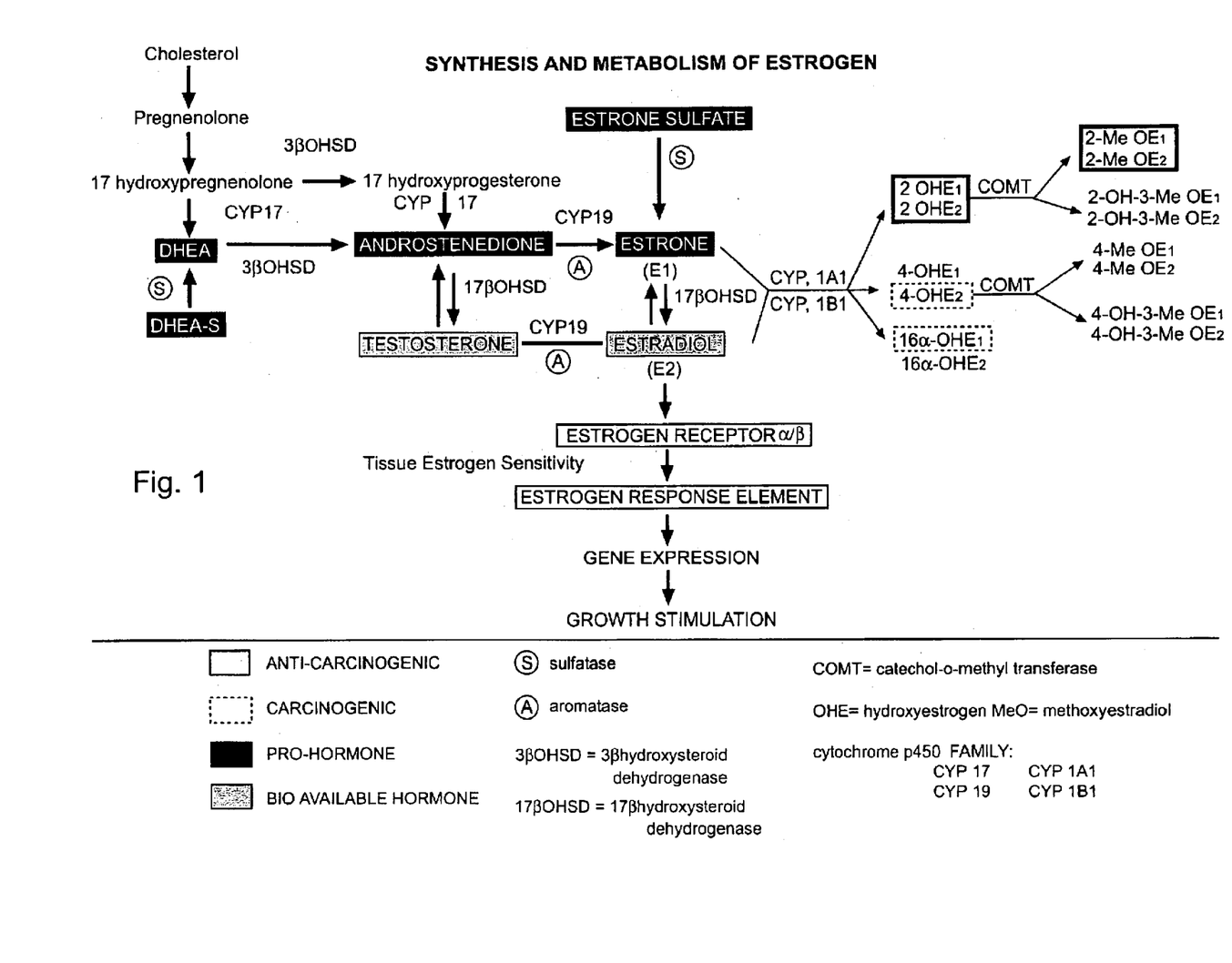
FIG. 1 summarizes the pathways of estrogen biosynthesis and metabolism.

In postmenopausal women, estrogen synthesis and metabolism takes place primarily in non-ovarian sites: adipose tissue, muscle, and liver. As illustrated in FIG. 1, the amount and type of estrogen synthesized is governed by three enzyme systems: (1) cytochrome p450 17α-hydroxylase/$C_{17-20}$ lyase activity is responsible for the production of dehydroepiandrosterone (DHEA) (from pregnenone); (2) 3β-hydroxysteroid dehydrogenase (3β-OHSD)-Δ5,4-isomerase catalyzes the conversion of DHEA to androstenedione; (3) p450 aromatase regulates the conversion of androstenedione to estrone, and testosterone to estradiol; while (4) 17β-hydroxysteroid dehydrogenase (17β-OHSD) modulates the bi-directional formation of androstenedione to testosterone, and estrone to the more potent estradiol.

The 17α-hydroxylase enzyme and the aromatase enzyme are both genetically controlled by cytochrome CYP17 and cytochrome CYP19, respectively. It has been found that women with CYP17 polymorphism have high serum estradiol values (Hairman, C. A. et al., "The relationship between a polymorphism in CYP17 with plasma hormone levels and breast cancer," *Cancer Res.*, 59:1015–1020 (1999)). The aromatase gene may, under certain biological conditions, act as an oncogene within breast tissue (Siegelmann-Danieli, N. and K. H. Butetow, "Constitutional genetic variation at the human aromatase gene (Cyp19) and breast cancer risk," *Br. J. Cancer*, 79:456–463 (1999)). Also, 17β-OHSD levels are higher in breast cancer compared with normal breast tissue, and may influence the course and progression of the disease by elevating local estrogen production (Vermeulen, A. et al., "Steroid dynamics in the normal and carcinomatous mammary gland," *J. Steroid Biochem.*, 25:799–802 (1986)).

The metabolism of estrogen follows pathways that result in either estrogenic or non-estrogenic metabolites. Estrogen catabolism takes place in two stages: hydroxylation and methylation. Estrone and estradiol are hydroxylated to the following: 2-hydroxyestrone (2-$OHE_1$), 2-hydroxyestradiol (2-$OHE_2$), 4-hydroxyestrone (4-$OHE_1$), 4-hydroxyestradiol (4-$OHE_2$), 16-hydroxyestrone (16-$OHE_1$), and 16-hydroxyestradiol (16-$OHE_2$). Women who preferentially metabolize their endogenous estrogens via the 16α-hydroxylation pathway (versus 2α-hydroxylation) are at higher risk of breast cancer (Ursin et al., "Urinary 2-hydroxyestrone/16alpha-hydroxyestrone ratio and risk of breast cancer in postmenopausal women," *J. Natl. Cancer Inst.*, 91:1067–1072 (1999)) as are women with elevated 4-hydroxylase activity in their breast tissue (Lieber, J. G. et al., "Adenovirus-mediated urokinase gene transfer induces liver regeneration and allows for efficient retrovirus transduction of hepatocytes in vivo," *Proc. Natl. Acad. Sci. U.S.A.*, 92(13):6210–4 (1995)). The hydroxylation of estrogen is genetically controlled: for example, the CYP1A1 gene, which encodes cytochrome p450 CYP1A1, inhibits or downgrades the activity of the 2α-hydroxy pathway, thereby diminishing the concentration of the benign protective 2-hydroxy estrogens in favor of the biologically potent 16-hydroxyestradiol metabolite (Huang et al., "Breast cancer risk associated with genotype polymorphism of the estrogen-metabolizing genes CYP17, CYP1A1, and COMT: a multigenic study on cancer susceptibility," *Cancer Res.*, 59:4870–4875 (1999)), while 4-hydroxylation is catalyzed via CYP1B1 (Hayes et al., "17 beta-estradiol hydroxylation catalyzed by human cytochrome p450 1B1," *Proc. Natl. Acad. Sci. U.S.A.*, 93:9776–9781 (1996)).

The 2- and 4-hydroxy metabolites are methoxylated via catechol-O-methyltransferase (COMT) activity into anticarcinogenic metabolites with little or no estrogen receptor binding affinity. There are significant variations among women in COMT activity. It has been postulated that women with lower COMT activity may be at higher risk of estrogen-associated breast cancer due to decreased formation of the anti-tumorugenic 2-methoxyestradiol and the retarded inactivation of the pro-angiogenic 4-OHE$_2$ metabolite (Zhu, B. J. and A. H. Conney, "Functional role of estrogen metabolism in target cells: review and perspectives," *Carcinogenisis*, 19:1–27 (1998)). Conversely, upregulation of 2-methoxyestradiol synthesis inhibits the proliferation of human breast cancer cell lines (in both estrogen receptor positive or negative breast cancer cells) and is a potent inhibitor of angiogenesis. Thus, factors, including hormone therapy, that either increase or decrease this estrogen metabolite, could have a profound influence on the pathogenesis of breast cancer (Chushman, M. et al., "Synthesis, antitubulin and antimitotic activity, and cytotoxicity of analogs of 2-methoxyestradiol, an endogenous mammalian metabolite of estradiol that inhibits tubulin polymerization by binding to the colchicine binding site," *J. Med. Chem.*, 38:2041–2049 (1995); Fotsis, J. et al., "2-methoxyestradiol, an endogenous estrogen metabolite, inhibits angiogenesis and suppresses tumor growth," *Nature*, 368:237–239 (1994)). Postmenopausal women with a variant COMT allele are at increased risk of breast cancer (Lavigne et al., "An association between the allele coding for a low activity variant of catechol-O-methyltransferase and the risk for breast cancer," *Cancer Res.*, 57:5493–5497 (1997)). In short, metaboliles such as 16α-OHE$_1$ are powerful estrogen agonists whereas metabolites such as 2-OHE$_1$ act as estrogen antagonists. It is unclear whether the absolute concentration of these metabolites determines the eventual biological effect on breast tissue, or whether it is the ratio between the two metabolites (2-OHE$_1$/16α-OHE$_1$) that is of greater importance (Lippert, T. H. et al., "Estradiol metabolism during oral and transdermal estradiol replacement therapy in postmenopausal women," *Horm. Metab. Res.*, 30(9):598–600 (1998)). The same may be true for the absolute amounts or ratios of other estrogen metabolites that may have competing oncogenic or anti-carcinogenic activity i.e., activity due to polymorphism in the COMT gene.

Estrone sulfate is formed by peripheral conversion from estradiol and estrone. Studies have documented that 65% of the estradiol and 54% of the estrone produced are converted to estrone sulfate (Ruder et al., "Estrone sulfate: production rate and metabolism in man," *J. Clin. Invest.*, 51:1020–1023 (1972)). In absolute terms, the circulating level of estrone sulfate is 10–25 times that of estrone and estradiol. Estrone sulfate thus functions as a major reservoir for estrone and estradiol (Lobo, R. A., "Androgen excess and the infertile woman," *Obstet. Gynecol. Clin. North Am.*, 14:143–167 (1987)). Sulfatases in various tissues (and especially the breast) reduce the inactive estrone sulfate to estrone. Estrone is subsequently reduced to estradiol by 17β-OHSD.

Sulfatase (and 17β-OHSD) activity in breast tissue is quantitatively greater than that of aromatase, and is especially high in women with breast cancer (Pasqualini, Jr. et al., "Concentrations of estrone, estradiol, and estrone sulfate and evaluation of sulfatase and aromatase activities in pre- and postmenopausal breast cancer patients," *J. Clin. Endocrinol. Metab.*, 81:1460–1464 (1996)). The persistence of significant levels of testosterone in postmenopausal women is due to the peripheral conversion of the adrenal androgen precursor DHEA-S (dehydroepiandrosterone sulfate) to DHEA (dehydroandrosterone) via sulfatase activity. Testosterone is bio-converted to estradiol (Zumoff B. et al., "Twenty-four-hour mean plasma testosterone concentration declines with age in normal premenopausal women," *J. Clin. Endocrinol. Metab.*, 80:1429–1430 (1995)). The contribution of the DHEA-S/DHEA prohormones to breast cancer is unknown, but both are significant substrates for breast tissue synthesis of estradiol. Excess aromatization of testosterone to estradiol is thought by some researchers to correlate significantly with the risk of hormone-induced breast cancer. Others believe that androgens normally inhibit mammary epithelial growth (Dimitrakakis, C. et al., "Androgens and mammary growth and neoplasia," *Fertil. Steril.*, 77(Suppl. 4):26–33 (2002)).

Although prolonged exposure of the breast tissue to estrogen is linked to an increased risk of breast cancer, identification of the individual at risk is problematic. Measuring serum estradiol levels provides some guidance, even though peripheral estradiol blood levels are substantially lower than breast tissue—and especially breast cancer tissue—levels (Pasqualini, Jr., et al., *J. Clin Endocrinol Metab* (1996)). The estradiol serum values associated with breast cancer risk are also much lower than previously accepted 'normal' postmenopausal estrogen blood level (Cauley, J. A. et al., *Ann. Intern. Med.*, (1999)). It is now possible to predict the estrogen receptor status of breast tumors using gene expression data with 90% accuracy (West, M. et al., "Predicting the clinical status of human breast cancer by using gene expression profiles," *Proc. Natl. Acad. Sci.*, 98:11–62–67 (2001)). In addition, for those who are found to be estrogen receptor positive, the individual breast tissue estrogen metabolite pathway, and the potential for breast cancer, could be identified by establishing the women's cytochrome p450 characteristics (Nebert, D. W. and D. W. Russell, "Clinical importance of the cytochromes P450," *Lancet*, 360:1155–1162 (2002)).

Genotyping of women at risk for breast cancer is a promising new approach. Polymorphism of cytochrome CYP17 (resulting in raised estrogen concentrations) and cytochrome CYP1A1 activity (inhibition of 2α-OHE$_1$ and 2α-OHE$_2$) and decreased COMT activity (decreased methoxylation of the potent OHE$_1$ metabolite) were, in one study, associated with an increased risk of breast cancer (Huang et al., *Cancer Res.* (1999)). Advances in gene technology now permit the measurement of candidate gene polymorphisms that alter in-situ estrogen synthesis in liver (COMT, CY1B1, CY1A1), in breast tissue (CYP1a, CYP1B1, CYP1A1), and the adrenal glands/ovaries (CYP17), and which will then allow for the selective use of microassay analysis to assess breast tissue expression of genes that metabolize hormones and which are clear indicators of the breast tissue's response to estrogen. This approach adopts the documented value of microarray analysis that has been developed as a predictor of the outcome of disease in young women with breast cancer (van de Vijver et al., "A gene-expression signature as a predictor of survival in breast cancer," N. Engl. J. Med., 347:1999–2009 (2002)), but allows for the early identification of women with high pro-carcinogenic estrogen metabolic profiles, and hence, the ability to selectively prescribe chemopreventive therapies such as sulfatase or aromatase inhibitors, and/or selective estrogen receptor modulators.

The impact of prescribed ERT, and its effect on the breast, is additive to the breast tissue pretreatment hormonal milieu. The 'dose' of estrogen that might initiate or promote the transformation of normal breast tissue to cancer is not known. However, there are women whose estrogen-sensitive target organs display an exaggerated response to physiological levels of estradiol.

The route of ERT may be important in women with certain estrogen metabolic polymorphism. An oral daily dose of 1 mg 17β-estradiol is considered to be equivalent, in terms of clinical efficacy, to biweekly 50 μg transdermal estradiol. This dose comparison may be misleading, however, because it does not account for large diffusion in estradiol metabolite concentrations nor does it account for the increase in sex hormone-binding globulin (SHBG) after oral, but not transdermal, ERT (Vehkavaara, S. et al., "Differential effects of oral and transdermal estrogen replacement therapy on endothelial function in postmenopausal women," Circulation, 102:2687–2693 (2000)). The long term consequences of this SHBG-binding variance has not been documented in clinical trials, but does account for many instances of 'non-response to adequate ERT' experienced by women in clinical practice.

Because of increased SHBG binding (and possibly other factors), more estrogen is needed after oral ERT to achieve a clinical response equivalent to that obtained by non-oral ERT. Only 5% of oral estradiol is bioavailable following the first-pass hepatic metabolism of oral estradiol. There is only minimal first-pass metabolism of non-oral estradiol (Kuhnz et al., "Pharmacokinetics of estradiol, free and total estrone, in young women following single intravenous and oral administration of 17 beta-estradiol," Arzneimittelforschung, 43:966–973 (1993)). Over time, the difference in hepatic modification of estradiol between the oral and transdermal routes is lessened.

When the gastric transit time and the enterohepatic recirculation of estrogen are factored in, oral estradiol therapy results in supraphysiological levels of estrone sulfate. This is reflected in a recent study summarized in the following Table 1 which compares the blood levels of the pro-hormone estrone sulfate, following equivalent doses of either oral or transdermal estradiol (Slater, C. C. et al., "Markedly elevated levels of estrone sulfate after long-term oral, but not transdermal, administration of estradiol in postmenopausal women," Menopause, 8:200–203 (2001)). Normal menstrual cycle levels of $E_1S$ were at 2–3 ng/mL. The clinical significance of prolonged supra-physiological levels of estrone sulfate is not known. Depending on the breast tissue sulfatase and 17β-OHSD activity, high concentrations of local breast tissue estradiol can be anticipated. The amount of estrone sulfate absorbed and metabolized after oral ERT may vary with the composition of the oral estrogen prescribed. Approximately 45% of the total dose of conjugated equine estrogens (CEE), 75–85% of esterified estrogen and 75% of piperazine sulfate is composed of estrone sulfate ((Slater et al, 2001, Menopause 8:200). Although a portion of estrone sulfate is hydrolyzed to estrone in the intestine, the unconjugated estrogen is reconjugated in the liver to the sulfate. Estrone sulfate is also subject to hepatic recirculation.

TABLE 1

Estrone Sulfate ($E_1S$) ng/mL Following Oral v. Transdermal Estradiol Endogenous $E_1S$ 10–25 > $E_1$ and $E_2$

| Test Interval | Estradiol 1 mg (oral) | Estradiol 50 mcg (TD) | Estradiol 100 mcg (TD) | Placebo patch |
|---|---|---|---|---|
| B | 0.80 | 0.70 | 0.80 | 0.80 |
| 1 | 25.00 | 1.60 | 2.30 | 1.00 |
| 2 | 39.00 | 1.80 | 3.20 | 1.20 |
| P | <0.01 | <0.05 | <0.05 | N/S |

Supraphysiologic breast tissue levels of estradiol, apart from directly inducing proliferation of ductal and epithelial elements of the breast, could via regulatory mutation alter the expression of a gene that leads to either a loss of function or to a positive expression in a tissue, in which it was previously silent (Guttmacher, A. E. and F. S. Collins, "Genomic medicine—a primer," N. Eng. J. Med., 347:1512–1520 (2002)).

BRIEF SUMMARY

The subject invention provides unique and advantageous methods for designing therapies to match the particular needs of individual menopausal or postmenopausal female patients. Specifically, in accordance with the subject invention, menopausal and postmenopausal women are evaluated for particular factors, including a dynamic breast endocrine metabolic profile, which are then taken into account in identifying a preferred therapy program to meet the needs of each particular woman, while reducing the likelihood of that woman developing adverse health effects as a result of the therapy.

Specifically exemplified herein is a system by which a woman who is a candidate for estrogen or hormone replacement therapy (ERT/HRT) is evaluated to ascertain specific information that is then used to determine whether such therapy is appropriate and, if so, the specifics of how that therapy is to be administered. In selected situations, this approach would also allow for the identification of women with an increased risk of breast cancer due to excessive endogenous breast tissue estrogen synthesis, which could be inhibited/normalized with appropriate specific therapies (i.e., the use of sulfatase or aromatase inhibitors, or selective estrogen receptor modulators).

In one aspect, the subject invention concerns evaluation methodologies used to identify women whose endogenous estrogen metabolism predisposes them to an increased risk of breast cancer. In another aspect, the subject invention identifies those women who would benefit from the use of chemopreventive agents (i.e., selective estrogen receptor modulators). In a further aspect, the subject invention concerns the modulation of the dose and route of HRT or ERT in order to lessen the risk of estrogen-promoted breast cancer in individuals who may be predisposed to such cancer or to institute treatment with breast estrogen metabolism modulators including, for example, sulfatase aromatase inhibitors, selective estrogen receptor modulators, and the like.

In a specific embodiment, the present invention provides a method wherein factors that influence estrogen metabolism are evaluated prior to initiating HRT. These and other factors are evaluated to determine the preferred therapy in order to reduce the risk of cancer. According to the subject invention, an individual is evaluated for appropriate menopausal or postmenopausal therapies.

In a related embodiment, the individual is assessed to determine whether she is at high risk for estrogen-promoted cancer, and whether this risk can be attenuated by modifying the proposed therapies. The modification to the proposed therapies can be designed to, for example, modulate the metabolism of endogenous estrogen by selectively inhibiting certain metabolic pathways of estrogen synthesis. In addition, since the risk of cancer may be dose dependent, the present invention provides treatment regimens based on the relative potencies and dose equivalence of standard doses of oral and transdermal estrogen.

The method according to the present invention includes obtaining a Breast Hormone Profile for an individual. The "Breast Hormone Profile," as used herein, refers to an evaluation of an individual's breast endocrine metabolism. A Breast Hormone Profile can be based on an evaluation of those factors that influence estrogen metabolism. For example, bioavailable hormones, pro-hormones (and substrates), and enzyme systems that are involved in the eventual synthesis and activity of estradiol and the cytochrome p450 genes that control the function of the relevant enzyme systems, all of these may be assessed in obtaining a Breast Hormone Profile. The Breast Hormone Profile allows for the identification of women who should selectively undergo a breast needle biopsy to provide tissue for a breast tissue metabolic profile, and to provide specific chemopreventive therapy and/or individualized low-dose hormone therapy.

In a preferred embodiment, therapy may be selected for either oral or transdermal administration based on the results of the Breast Hormone Profile, and when necessary, from the results of a breast needle biopsy. For example, either low-dose oral or transdermal estrogen therapy would be appropriate in women with normal estradiol levels and normal substrate concentrations, enzyme activities, and estrogen metabolism. Transdermal estrogen therapy, because of its reduced post-absorption metabolism, may be applicable for women with high serum estrone sulfate, androstenedione, and estrone levels.

In one embodiment, the method according to the present invention includes the steps of conducting a diagnostic quality mammogram, genotyping for at least one enzyme system that regulates hormone biosynthesis and metabolism and breast estrogen receptor status; and obtaining a Breast Hormone Profile.

In a preferred embodiment, the method according to the present invention includes the steps of:

1) gathering appropriate reproductive and family history;
2) conducting a comprehensive physical examination;
3) conducting a diagnostic quality mammogram and conducting a bone density test (BMD);
4) genotyping enzyme systems that regulate hormone biosynthesis and metabolism and breast estrogen receptor status;
5) evaluating breast endocrine metabolism; and
6) conduction a breast biopsy.

The present invention provides methods that differentiate risk factors for a disease to prescribe appropriate menopausal and postmenopausal therapies that promote good health and avoid/minimize adverse health events, such as breast cancer. For example, by assaying candidate genes and using microarray analysis techniques to identify those genes that control or mediate estrogen biosynthesis and metabolism, genetic traits emerge that can be linked to other genetic or environmental factors (i.e., HRT) that are known to increase the risk of breast cancer in susceptible women. Such assaying technologies, together with the measurement of relevant bio-active hormones (i.e., estradiol, testosterone) and their precursor pro-hormones (androstenedione, estrone sulfate, estrone and the respective estrogen metabolites) form the basis of the invention.

Accordingly, the invention facilitates designing treatment so that patients receive the lowest dose of bioavailable hormones by either the oral or transdermal route based on the manner in which they metabolize their prescribed hormones. Such individualized treatment assists in decreasing the risk of cancer. The invention further facilitates designing prescription therapies (sulfatase/aromatase inhibitors) that reduce and/or normalize the amount of endogenous estrogen (estradiol) synthesized in breast, adipose tissue or muscle.

In one embodiment, tests that include the genetic profiling, measurement of bioavailable hormones and pro-hormones, and relevant estrogen metabolites are performed on single samples of blood and urine. Samples are collected at the initial evaluation before treatment is prescribed. Depending on the Breast Hormone Profile results, therapies relevant to the patient's needs are prescribed. For example, a woman assessed as being at a high risk for cancer may be prescribed chemopreventive agents. These include low-dose oral or transdermal sulfatase or aromatase inhibitors, a selective estrogen receptor modulator (SERM), or a combination of the above. Follow-up testing approximately three months after initiation of a specific regimen may include all of the hormonal tests, or be restricted to those parameters that were found to be abnormal on base-line testing. Based on the patient's response at the three month evaluation, the Breast Hormonal Profile or selective components of the Breast Hormonal Profile (and when necessary, a breast biopsy), will be repeated at annual intervals to assess both the efficacy and the safety of the selected initial therapy. This is advisable since the prescribed therapy or other environmental factors could alter the functional expression of some of the genes governing breast endogenous hormone synthesis and metabolism.

DETAILED DISCLOSURE

The subject invention provides unique and advantageous methods for designing therapies to match the particular needs of individual patients. Specifically, in accordance with the subject invention, menopausal and postmenopausal women are evaluated for particular factors that are taken into account in assessing a preferred therapy program to meet the needs of each particular woman, while reducing the likelihood of that woman developing adverse health effects as a result of therapy. Specifically exemplified herein is a system by which a woman who is a candidate for hormone replacement therapy is evaluated to ascertain specific information that is used to determine whether such therapy is appropriate and, if so, the specific route that therapy is to be administered.

DEFINITIONS

The "Breast Hormone Profile," as used herein, refers to an evaluation of an individual's breast endocrine metabolism.

A breast biopsy (or breast metabolism biopsy), as contemplated herein, refers to any method of removing a breast tissue sample for histologic examination. Common types of breast biopsies include, but are not limited to, open excisional biopsy, axillary node dissection, sentinel node dissection, and needle aspiration. According to the subject invention, the results from a breast biopsy can be used in evaluating breast tissue estrogen metabolism.

A mammogram, as contemplated herein, refers to any diagnostic imaging of breast tissue. For example, x-rays or ultrasound may be used to create images of breast tissue for clinical analysis. According to the present invention, a screening mammogram is utilized to assess breast density in menopausal or postmenopausal patients. The results of the mammogram, in combination with other factors, are taken into account in assessing a preferred therapy program for each patient.

The term "genotyping," as used herein, refers to the detection of specific genes. A variety of genotyping techniques are available (see Kristensen V N, et al., "High-throughput methods for detection of genetic variation," *Biotechniques*, (2):318–22, 324, 326 passim (2001)). In accordance with the subject invention, techniques for identifying specific genes include, but are not limited to: (a) enzymatic approaches, in which the properties of different enzymes to discriminate between nucleotides are used (i.e., restriction fragment length polymorphism (RFLP), amplified fragment length polymorphism (AFLP), cleavase fragment length polymorphism analysis, invasive cleavage of nucleotide probes, ligase detection reaction, random amplified polymorphic DNA, and directed termination PCR); (b) electrophoretic methods, in which the allele discrimination is based on the difference in mobility in polymeric gels or capillaries (i.e., single-strand conformation polymorphism, heteroduplex analysis, fragment analysis, and high-performance DNA sequencing); (c) solid-phase determination of allelic variants, including high density oligonucleotide arrays for hybridization analysis, minisequencing primer extension analysis, and fiberoptic DNA sensor array; (d) chromatographic methods; and (e) other physical methods such as mass spectrometry. In one embodiment of the subject invention, microarray assay technology is utilized to detect CYP gene polymorphism.

Table II summarizes some of the bioavailable hormones, pro-hormones (and substrates), and enzyme systems that are involved in the eventual synthesis and activity of estradiol and the cytochrome p450 genes that control the function of the relevant enzyme systems and breast tissue estrogen metabolism. Measurement and clinical interpretation of these parameters form the basis of the Breast Hormone Profile and aid in determining whether to perform a breast biopsy.

The free testosterone represented in Table II is the hormone present in blood is measured by assessing the total amount of testosterone versus the amount of sex hormone binding-globulin (SHBG). Free estradiol present in blood is measured by assessing the total amount of estradiol versus the amount of SHBG. COMT is to be assayed if 2-methoxyestradiol levels are low in women with increased mammographic density. Microarray assay technology for detecting CYP gene polymorphism can be used to identify aberrant peripheral (breast) tissue estrogen metabolism in women with suspect hormonal profiles and/or mammographic results.

TABLE II

Breast Hormone Profiling Sequential Clinical Testing Paradigm

|  | BLOOD | URINE | GENES Polymorphism |
|---|---|---|---|
| 1st TIER | Estradiol (E$_2$) (high sensitivity) Free Testosterone (T) (Total T/SRBC) Estradiol (Total E$_2$/SHBG) | 2-OH Estrone 2-OH Estradiol 4-OH Estrone 4-OH Estradiol 16-OH Estrone 16-OH Estradiol 2-Methoxyestrone 2-Methoxyestradiol | CYP 17 CYP 19 CYP1A1 CRYP 1B1 3β-HSD 17β-HSD |
| 2nd TIER | Estrone Estrone Sulfate Androstendione COMT |  | Microarray breast tissue gene-expression analysis |
| 3rd TIER | DHEA DHEA-S |  |  |

In one embodiment of the subject invention, the measurement and clinical interpretation of the parameters identified in Table II assist in designing an appropriate therapy for an individual patient. For example, where women demonstrate normal estradiol values, normal substrate concentrations, enzyme activities, and estrogen metabolism, low dose estrogen or hormone therapy may be administered to a patient. For women with high-quartile (but normal) serum values of estradiol combined with elevated plasma estrone sulfate, appropriate therapy can include ERT or HRT treatment in combination with sulfatase inhibitors such as tibolone. Where androstenedione levels are abnormal, treatment may include the administration of aromatase inhibitors, including synthetic androgens such as methyl testosterone. Where unexplained high levels of estradiol are found or in the presence of clinically demonstrable peripheral-tissue estradiol sensitivity (increased breast tissue density, high bone mineral density, low-normal serum estradiol), therapy may include selective estrogen receptor modulators (SERMs), with or without low-dose transdermal add-back therapy. In certain instances, a breast metabolism biopsy can assist in determining the most appropriate therapeutic approach.

In addition, based on the results of the screening method, therapy may be selected for either oral or transdermal administration. For example, either low-dose oral or transdermal estrogen therapy would be appropriate in women with normal estradiol levels and normal substrate concentrations, enzyme activities, and estrogen metabolism. Transdermal estrogen therapy, because of its reduced post-absorption metabolism, may be applicable to women with high serum estrone sulfate, androstenedione and estrone levels.

In one embodiment, the method according to the present invention includes the steps of conducting a diagnostic quality mammogram, genotyping enzyme systems that regulate hormone biosynthesis and metabolism and breast estrogen receptor status; and obtaining a hormone profile.

In a preferred embodiment, the method according to the present invention includes the steps of:

1) gathering appropriate reproductive and family history;
2) conducting a comprehensive physical examination;
3) conducting a diagnostic quality mammogram and conducting a bone density test (BMD);
4) genotyping enzyme systems that regulate hormone biosynthesis and metabolism and breast estrogen receptor status;
5) obtaining a hormone profile; and
6) conducting a selective breast metabolism biopsy.

By utilizing this method, the present invention provides for a more specific and individualized approach to treating women using HRT or ERT based on an individualized assessment of the risk of breast cancer.

The present invention relies on methods that differentiate risk factors for a disease, rather than the presence of a disease. By assaying candidate genes and through the use of microarray analysis techniques (van de Vijver et al., "A gene-expression signature as a predictor of survival in breast cancer," N. Engl. J. Med., 347:1999–2009 (2002)) for identifying genes that control or mediate estrogen biosynthesis and metabolism, genetic traits emerge that can be linked to other genetic or environmental factors that are known to increase the risk of breast cancer in susceptible women. Such technologies, together with the measurement of relevant bio-active hormones (i.e., estradiol, testosterone) and their precursor pro-hormones (androstenedione, estrone sulfate, estrone and the respective estrogen metabolites) form the basis of the invention as a dynamic "breast function test."

In accordance with the present invention, individualized therapies can be designed to aid in preventing the development of breast cancer in patients. For example, patients assessed with dysfunctional or aberrant estrogen biosynthesis (a risk-factor for breast cancer) can accordingly be provided specific therapies that can correct/inhibit the breast tissue metabolic abnormality. Thus, breast cancers can be prevented by this approach as opposed to treating the disease after its development.

Accordingly, the invention facilitates designing therapies for patients to receive the lowest dose of bioavailable hormones by either the oral or transdermal route based on the manner in which they metabolize their prescribed hormones. Thus, such individualized therapies can be used to decrease the risk of cancer. The present invention also facilitates designing therapies (i.e., prescribing sulfatase/aromatase inhibitors) that will reduce and/or normalize the amount of endogenous estrogen (estradiol) synthesized in breast, adipose tissue or muscle.

According to the subject invention, the tests that include the genetic profiling, measurement of bioavailable hormones and pro-hormones, and relevant estrogen metabolites (see Table III) can be performed on single samples of blood and urine. In addition, blood and breast tissue samples can be tested for expression levels of CYP p450 genes. Bioavailable testosterone, as identified in Table III, include those that are freely available versus those bound by sex hormone binding globulin (SHBG). Samples can be collected at the initial evaluation before treatment is prescribed. Depending on the patient's Breast Hormone Profile, therapies relevant to the patient's needs are prescribed. These may include low-dose oral or transdermal estrogen, sulfatase or aromatase inhibitors, a selective estrogen receptor modulator (SERM), or a combination of the above. Follow-up testing three months after initiation of a specific regimen may include all of the hormonal tests, or be restricted to those parameters that were found to be abnormal on base-line testing. Based on the patient's response at the three month evaluation, the Breast Hormonal Profile or selective components of the Breast Hormonal Profile (and when necessary, a breast biopsy) will be repeated at annual intervals to assess both the efficacy and the safety of the selected initial therapy. This is advisable since the prescribed therapy or other environmental factors could alter the functional expression of some of the genes governing breast endogenous hormone synthesis and metabolism.

TABLE III

Clinical Breast Hormone Profile Relevant to Breast Cancer Risk

| Pro-Hormones | Enzymes | Bio-Available Hormones | Estrogen Metabolites | CYP p450 Genes |
|---|---|---|---|---|
| DHEA | Aromatase | Estradiol | 2OH-Estrone | CYP 17 |
| Androstenedione | Sulfatase | (Free $E_2$/SHBG) | 2OH-Estradiol | CYP19 |
| Estrone | 3β-Hydroxysteroid dehydrogenase | Testosterone (Free T/SHBG) | 4OH-Estradiol | CYP1A1 |
|  | 17β-Hydroxysteroid dehydrogenase |  | 16αOH-Estrone | CYP1B1 |
|  | COMT |  | 2-methoxyestradiol |  |

By way of example, a woman assessed as being at a high risk for cancer may be prescribed chemopreventive agents. These may include low-dose oral or transdermal sulfatase or aromatase inhibitors, a selective estrogen receptor modulator (SERM), or a combination of the above. Follow-up testing three months after initiation of a specific regimen can include hormonal tests, or be restricted to those parameters that were found to be abnormal on base-line testing. Based on the patient's response at the three month evaluation, the Breast Hormonal Profile or selective components of the Breast Hormonal Profile (and when necessary, a breast biopsy), will be repeated at annual intervals to assess both the efficacy and the safety of the selected initial therapy.

Figure 2:
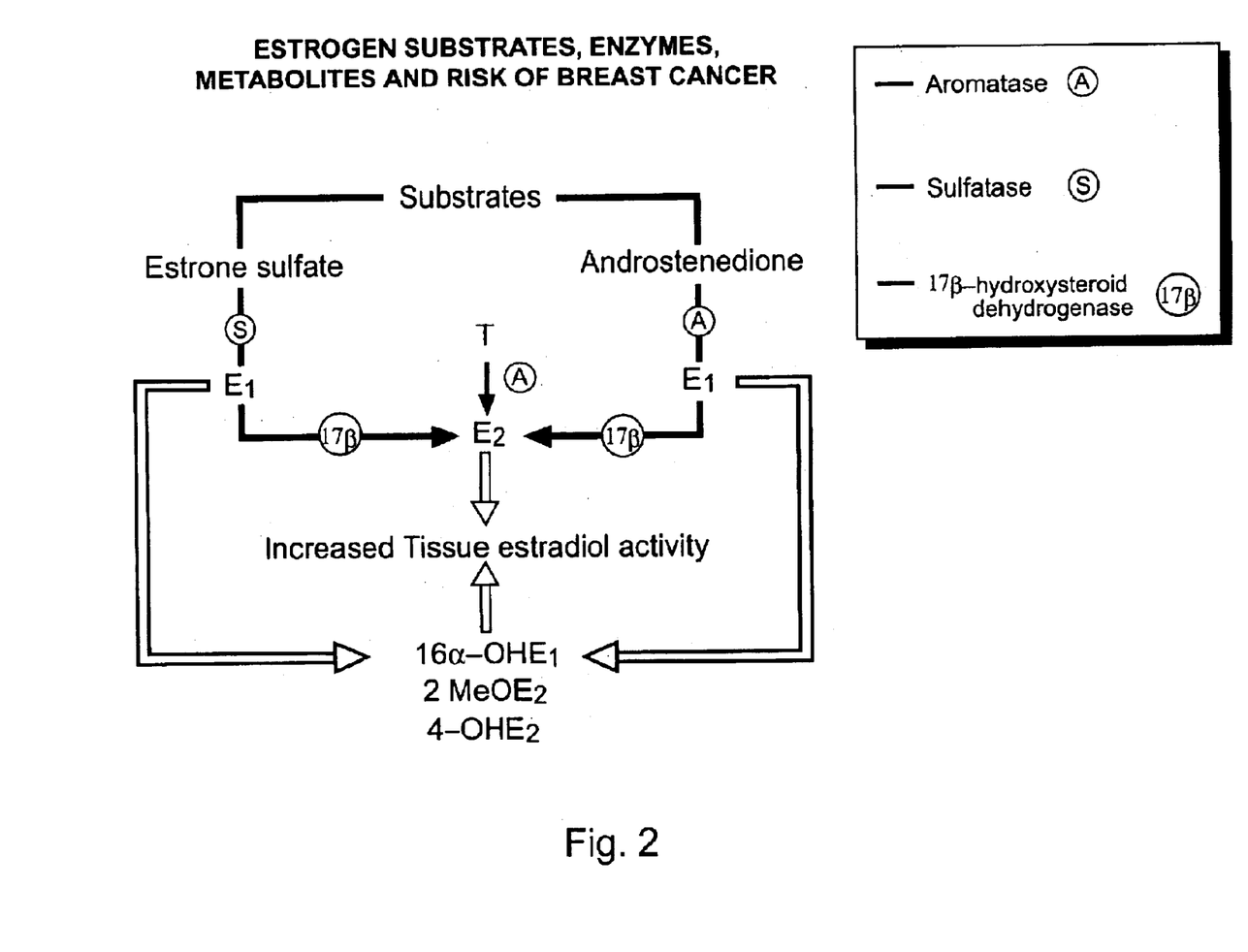
FIG. 2 illustrates the relationship between estrogen substrates, enzymes, and metabolites and the risk of cancer.
Figure 3:
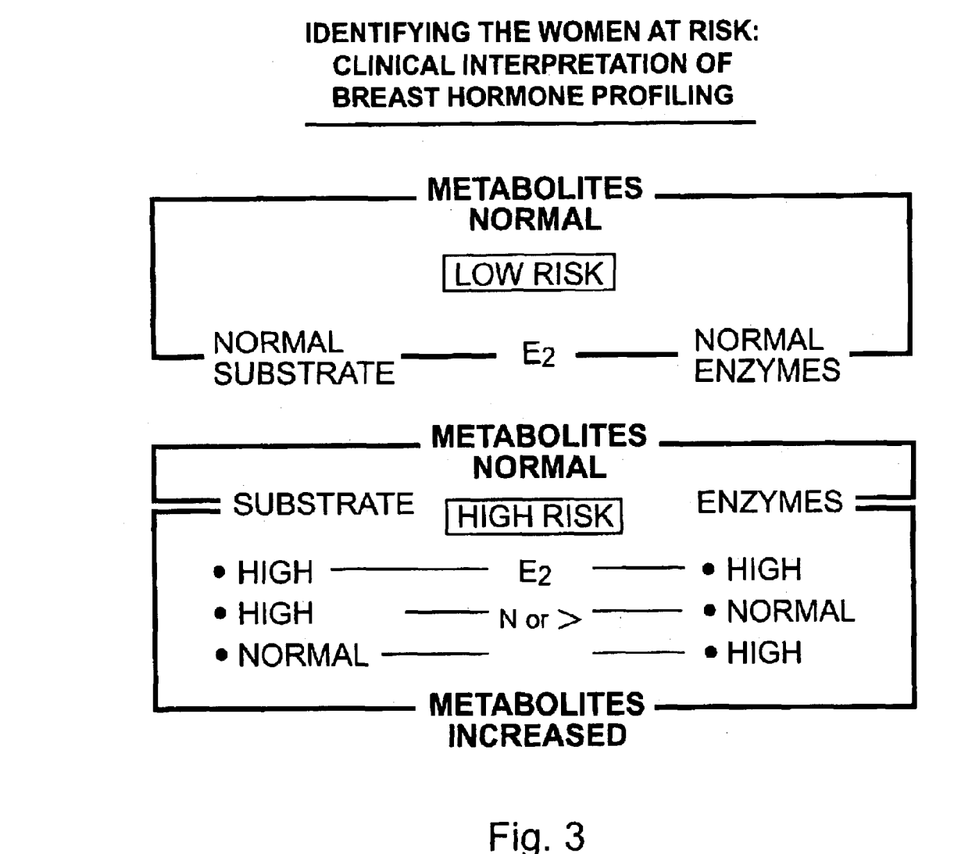
FIG. 3 is a chart summarizing the classification of patients based on the interaction of estrogen substrate-enzyme-metabolites.
Figure 4:
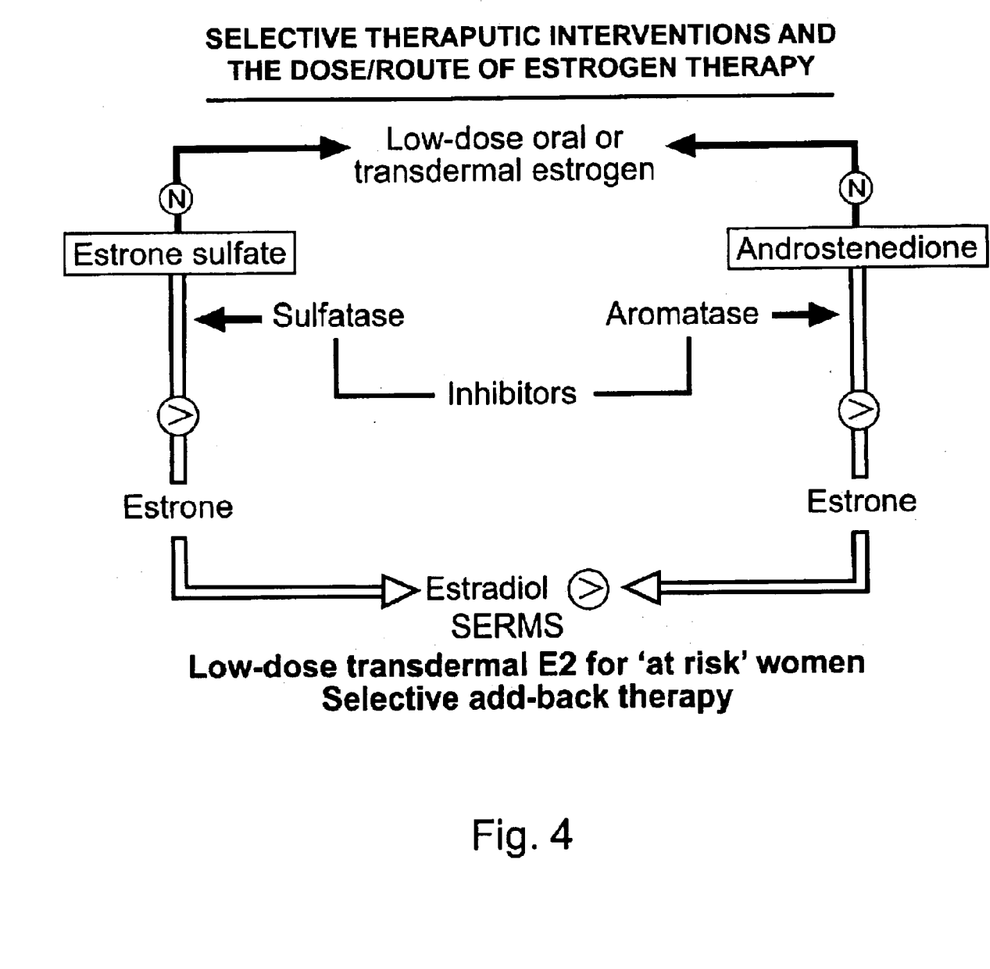
FIG. 4 is a chart summarizing appropriate therapeutic interventions and dose/route of estrogen therapy based on the identification and assessment of certain factors specific to each patient.

A means for establishing a risk for developing breast cancer is illustrated in FIG. 2, wherein a hormone profile includes the results from a baseline high-sensitivity estradiol test correlated with the assay of three precursor estradiol hormones plus an estimation of urinary secretion of $2\text{-OHE}_1$, $16\alpha\text{-OHE}_1$, and $4\text{-OHE}_2$ metabolites, and $2\text{-MeOE}_2$. Based on these parameters, a Breast Metabolism Biopsy may be performed, and patients classified into the hormonal categories summarized in FIG. 3. This permits the selection of therapy for high-risk women specific to their underlying hormonal dysfunction. Some selective therapeutic interventions based on hormonal categories are illustrated in FIG. 4.

Figure 5:
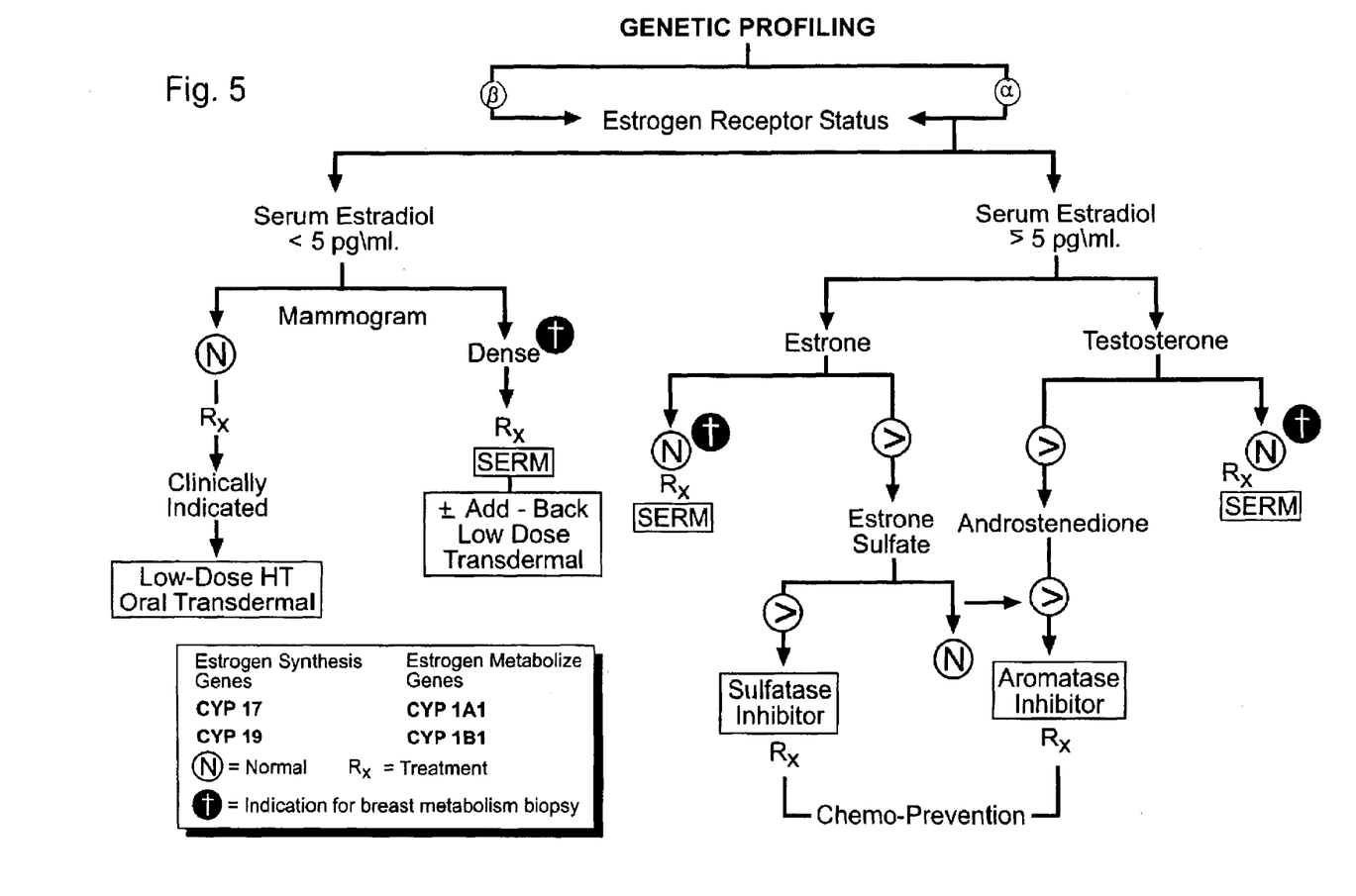
FIG. 5 is a chart summarizing the use of the Breast Hormone Profile test to aid in selecting an appropriate therapy for a patient.

In a preferred embodiment, the subject invention involves conducting a diagnostic mammogram, genotyping at least one enzyme system that regulates hormone biosynthesis and metabolism, and obtaining a hormone profile to discriminate between postmenopausal women who are at different risks for developing breast cancer. This profile, as illustrated in FIG. 5, can include the correlation of gene detection (i.e., estrogen synthesis genes to establish estrogen receptor status), and clinical features (increased breast density on mammography images, increased BMD), with a baseline high-sensitivity serum estradiol test, the assay of precursor estradiol hormones—serum testosterone, androstenedione, estrone, and estrone sulfate—plus metabolites of estrogen. In a preferred embodiment, genotyping is conducted for estrogen synthesis and estrogen metabolizing genes, a mammogram is conducted, and a Breast Hormone Profile is obtained. An individualized therapy is then provided based on the results of the genotyping, the mammogram, and the Breast Hormone Profile. For example, as illustrated in FIG. 5, when mammogram results are normal and the patient's estradiol serum level is less than 5 pg/mL, the individualized therapy for the patient can include low-dose, oral or transdermal administration of hormone replacement therapy.

Women with high-quartile serum values of estradiol combined with elevated plasma estrone and estrone sulfate are preferably treated with sulfatase inhibitors (for example tibolone); aromatase inhibitors are chosen when androstenedione/testosterone levels are abnormal, and selective estrogen receptor modulators (SERMs) in situations where unexplained high estradiol values are found (all other tests being normal) or in the presence of clinically demonstrable peripheral-tissue estradiol sensitivity, for example dense breasts on mammography, high BMD, and low to normal serum estradiol levels.

A further embodiment involves the genotyping of the breast estrogen receptor status, the enzyme systems (i.e., cytochromes CYP17, CYP19, CYP1A1, and CYP1B1) that regulate hormone biosynthesis and metabolism, as well as the COMT activity of red blood cells, as part of a woman's pretreatment hormone profile. Genotyping can also be useful in determining whether a patient should undergo a breast biopsy. Genotyping helps to target the site of an abnormal endocrine pathway, and can improve the accuracy and specificity of the treatment decision.

Either low-dose oral or transdermal estrogen therapy, when clinically indicated, are appropriate in women with normal estradiol values, and normal substrate concentrations, enzyme activities and estrogen metabolism. Transdermal estrogen therapy is preferred: in women with high serum estrone sulfate and estrone levels; in those with increased $16\alpha OHE_1$ and $4\text{-}OHE_2$ metabolites; and, selectively, as add-back therapy in certain situations when SERMs, and aromatase inhibitors, are prescribed. Oral estradiol may be the preferred route of ERT/HRT together with aromatase inhibitors when testosterone levels are elevated. Oral ERT increases SHBG and decreases the bioavailability of testosterone. Given the variability of endogenous and exogenous estrogen metabolism, it is prudent to select a dose and route of ERT that results in a hormonal milieu that replicates the hormonal environment of normal breast tissue. Low-dose transdermal estrogen therapy has a metabolic profile that most closely fits this objective.

The present invention provides a method for screening individuals, using surrogate markers of breast tissue biology and function, to provide appropriate treatment for menopausal symptoms while reducing the risk of cancer. The method can include the steps of gathering reproductive and family history for breast cancer; conducting a comprehensive physical examination, including breast examination and determination of body mass index and waist/hip ratio; administering a diagnostic quality mammogram (and bone mineral density test); obtaining a breast function hormone profile, and when necessary, conducting a breast metabolism biopsy. From the combination of these steps, it is then possible to identify patients who may be at low or high risk of cancer.

A Breast Hormone Profile can include the assessment of a patient's: serum estradiol levels; estrone levels, estrene levels, estrone sulfate levels, androstenedione levels, testosterone levels; estrogenic and non-estrogenic urinary metabolite levels (i.e., $2OHE_1$; $16\text{-}OHE_1$, $4\text{-}OHE_2$, and $2MeOE_2$). For example, a high risk breast cancer hormone profile for a menopausal patient may be captured by measuring baseline high sensitivity serum estradiol levels and correlating the serum estradiol levels with the ratio between estradiol metabolites (i.e., $2\text{-}OHE_1/16\alpha\text{-}OHE_1$) or any one of the other pro-hormones, estrogen metabolites, cytochrome p450 genes or COMT activity noted previously, and/or an abnormal breast metabolism biopsy.

Assessing the risk for breast cancer can include: an appropriate reproductive and family history for breast cancer; a comprehensive physical examination (including breast examination and determination of body mass index and waist/hip ratio), a diagnostic quality mammogram; and, selectively, a high-sensitivity estradiol test. A bone mineral density (BMD) test can also be conducted. A normal to high BMD may be indicative of enhanced systemic endogenous estrogen synthesis, indicating preference for low-dose ERT. Low BMD allows for selection of the lowest dose of ERT appropriate for the degree of osteopenia rather than a generic 'standardized dose' of ERT.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method for providing an individualized therapy for a menopausal or postmenopausal patient, wherein said method comprises
    conducting a diagnostic mammogram;
    genotyping at least one enzyme system that regulates hormone biosynthesis and metabolism;
    evaluating breast endocrine metabolism; and
    based on the results of these tests, providing the individualized therapy to the patient.

2. The method according to claim 1, wherein the individualized therapy is a hormonal replacement therapy that treats conditions associated with menopause and postmenopause.

3. The method according to claim 1, wherein the individualized therapy is a hormonal replacement therapy that reduces the likelihood of developing future adverse health effects in the patient.

4. The method according to claim 1, wherein the step of evaluating breast endocrine metabolism comprises conducting a test for at least one bio-active hormone.

5. The method according to claim 4, wherein the bio-active hormone is estradiol.

6. The method according to claim 5, further comprising correlating the results of the mammogram with the results of the test for estradiol.

7. The method according to claim 6, wherein when the mammogram results are normal and the estradiol serum level is less than 5 pg/mL, the individualized therapy for the patient comprises low-dose, oral or transdermal administration of hormone replacement therapy.

8. The method according to claim 6, wherein when the results of the mammogram are highly dense tissue and the estradiol serum level is less than 5 pg/mL, the individualized therapy for the patient comprises administering selective estrogen receptor modulators.

9. The method according to claim 8, further comprising the step of administering low-dose, oral or transdermal hormone replacement therapy in combination with selective estrogen receptor modulators.

10. The method according to claim 8, further comprising the step of conducting a breast metabolism biopsy.

11. The method according to claim 4, further comprising conducting a test for at least one pro-hormone when the bio-active hormone level is too high.

12. The method according to claim 11, wherein the bio-active hormone is estradiol and the pro-hormone is estrone.

13. The method according to claim 12, wherein when the estradiol serum level is greater than or equal to 5 pg/ml and the estrone level is normal, the individualized therapy for the patient comprises administering selective estrogen receptor modulators to the patient.

14. The method according to claim 13, further comprising the step of conducting a breast metabolism biopsy.

15. The method according to claim 12, wherein when the estradiol serum level is greater than or equal to 5 pg/ml and the estrone level is higher than normal, an estrone sulfate level is assessed.

16. The method according to claim 15, wherein when the estrone sulfate level is above normal levels, the individualized therapy for the patient comprises administering sulfatase inhibitors to the patient.

17. The method according to claim 15, wherein when the estrone sulfate level is normal, the individualized therapy for the patient comprises administering an aromatase inhibitor to the patient.

18. The method according to claim 11, wherein the bio-active hormone is estradiol and the pro-hormone is testosterone.

19. The method according to claim 18, wherein when the estradiol serum level is greater than or equal to 5 pg/ml and the testosterone level is normal, the individualized therapy for the patient comprises administering selective estrogen receptor modulators to the patient.

20. The method according to claim 19, further comprising the step of conducting a breast metabolism biopsy.

21. The method according to claim 18, wherein when the estradiol serum level is greater than or equal to 5 pg/ml and the testosterone level is higher than normal, an androstenedione level is assessed.

22. The method according to claim 21, wherein when the androstenedion level is greater than normal, the individualized therapy for the patient comprises administering aromatase inhibitors to the patient.

23. The method according to claim 1, wherein the individualized therapy is a low-dose oral hormonal replacement therapy.

24. The method according to claim 1, wherein the individualized therapy is a low-dose transdermal hormonal replacement therapy.

25. The method according to claim 1, further comprising the step of gathering from the patient information regarding reproductive and family history.

26. The method according to claim 1, further comprising the step of conducting a comprehensive physical examination.

27. The method according to claim 1, further comprising the step of administering to the patient a bone mineral density test.

28. The method according to claim 1, further comprising the step of conducting a breast metabolism biopsy.

29. A method for providing an individualized therapy for a menopausal or postmenopausal patient, wherein said method comprises gathering from the patient information regarding reproductive and family history;

conducting a comprehensive physical examination;

conducting a diagnostic mammogram;

administering to the patient a bone mineral density test;

genotyping breast estrogen receptor status;

evaluating breast endocrine metabolism;

conducting a breast metabolism biopsy; and based on these results of these tests, providing the individualized therapy to the patient.

30. A method for providing an individualized therapy for a menopausal or postmenopausal patient, wherein said method comprises gathering from the patient information regarding reproductive and family history;

conducting a comprehensive physical examination;

conducting a diagnostic mammogram;

administering to the patient a bone mineral density test;

genotyping breast tissue expression levels of genes that determine the responsiveness of breast tissue to estrogen;

evaluating breast endocrine metabolism; and based on the results of these tests, providing the individualized therapy to the patient.

31. The method according to claim 30, wherein the genotyping includes testing estrogen receptor status.

32. The method according to claim 30, further comprising the step of conducting a breast metabolism biopsy.

* * * * *